(12) United States Patent
Hsu et al.

(10) Patent No.: US 7,671,328 B2
(45) Date of Patent: Mar. 2, 2010

(54) METHOD OF PRODUCING MOLECULAR PROFILES OF ISOPARAFFINS BY LOW EMITTER CURRENT FIELD IONIZATION MASS SPECTROMETRY

(75) Inventors: Chang Samuel Hsu, Warrenville, IL (US); Gary J Dechert, Asbury, NJ (US); Haven S. Aldrich, Baton Rouge, LA (US); Gerald D. Dupre, Clinton, LA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 341 days.

(21) Appl. No.: 11/702,830

(22) Filed: Feb. 6, 2007

(65) Prior Publication Data

US 2007/0181796 A1  Aug. 9, 2007

Related U.S. Application Data

(63) Continuation-in-part of application No. 09/521,072, filed on Mar. 7, 2000, now abandoned.

(51) Int. Cl.
*B01D 59/44* (2006.01)
*H01J 49/00* (2006.01)

(52) U.S. Cl. .................................. 250/282; 250/281
(58) Field of Classification Search .............. None
See application file for complete search history.

(56) References Cited

U.S. PATENT DOCUMENTS 5,644,129 A * 7/1997 Hsu et al. ............... 250/282

OTHER PUBLICATIONS

Jose C. Del Rio, et al., "Field ionization mass spectrometric study of high molecular weight hydrocarbons in crude oil and a solid bitumen", *Organic Geochemistry* 30 (1999), pp. 279-286.

* cited by examiner

*Primary Examiner*—David A Vanore
(74) *Attorney, Agent, or Firm*—Paul E Purwin; Liza Montalvo

(57) ABSTRACT

The present invention is devoted to an analytical method for directly determining carbon number and molecular weight distributions of isoparaffin mixtures. The analytical means uses low in-scan emitter-current field-ionization mass spectroscopy to substantially reduced or eliminated molecular ion fragmentation for isoparaffins, which allows direct measurement of isoparaffin molecular ions for their distributions. The analytical means is capable of directly characterizing isobutane to $C_{50}+$ isoparaffins, covering naphtha to gas oil ranges.

9 Claims, 12 Drawing Sheets

Field Ionization Mass Spectrum Of A
Low Boiling Isoparaffin Product,
Isopar G, At A Low Emitter Current (6 mA)

GC/ MS Chromatograms of a
Low Boiling Isoparaffin Product, Isopar G

Field Ionization Mass Spectrum Of A
Low Boiling Isoparaffin Product,
Isopar G, At A Low Emitter Current (6 mA)

Field Ionization Mass Spectrum Of A
High Boiling Isoparaffin Product,
Isopar V, At A Low Emitter Current (6 mA)

METHOD OF PRODUCING MOLECULAR PROFILES OF ISOPARAFFINS BY LOW EMITTER CURRENT FIELD IONIZATION MASS SPECTROMETRY

This application is a Continuation-in-Part of U.S. Ser. No. 09/521,072 filed Mar. 7, 2000, revived by Petition granted Mar. 4, 2008 now abandoned.

BACKGROUND OF THE INVENTION

Field Ionization Mass Spectrometry (FIMS) is well suited to hydrocarbon analysis. For normal paraffins and naphthenes, FIMS may be used to empirically determine the distribution of hydrocarbons as a function of carbon number or molecular weight. Their concentrations can be determined from relative ion abundance or peak intensities in the FIMS spectra. For example, U.S. Pat. No. 5,644,129 teaches the use of FIMS for just such a purpose. FIMS has also been found useful in the study of high molecular weight hydrocarbons. See for example, Field Ionization Mass Spectrometric Study of High Molecular Weight Hydrocarbons in a Crude Oil and a Solid Bitumen, Jose C. de Rio et al, Organic Geochemistry 30 (1999).

FIMS has not, however, been successfully used for the direct determination of the carbon number or molecular weight distribution of isoparaffins.

Conventional electron—impact ionization and even chemical ionization produce extensive fragmentation of isoparaffins, resulting in the absence of molecular or pseudo-molecular ions in the mass spectra. Conventional field ionization techniques such as those used in U.S. Pat. No. 5,644,129 also result in a high percentage of isoparaffin molecular ions being broken apart to form fragment ions. The carbon number distribution of isoparaffins is, therefore, currently estimated by comparing their retention times eluting off a non-polar "boiling point" gas chromatographic column with those of normal paraffins. Due to substantial overlap of components and broad distributions of isoparaffins, such estimation techniques are often not accurate.

This invention has discovered a means for producing intact molecular ions for isoparaffins for direct mass measurement.

SUMMARY OF THE INVENTION

The present invention is a method for directly measuring the carbon numbers and molecular weights of isoparaffins using field ionization mass spectroscopy. The in-scan emitter current is lowered to below a threshold value that would substantially reduce or eliminate fragmentation of isoparaffin molecular ions.

DETAILED DESCRIPTION OF THE INVENTION

Figure 1:
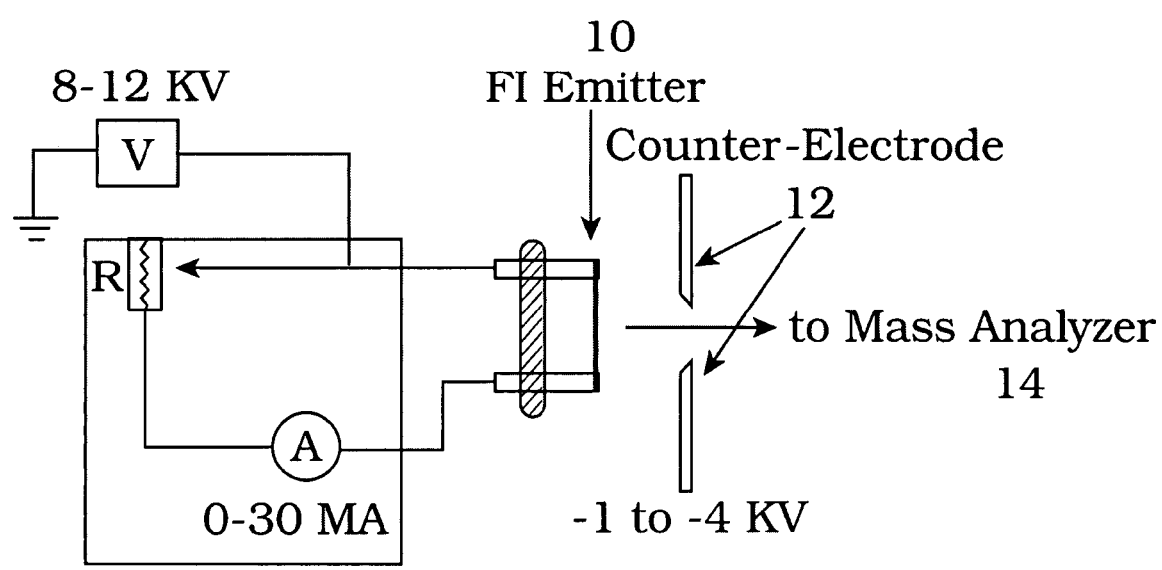
FIG. 1 shows a diagram of a field ionization mass spectrometer.
Figure 2A:
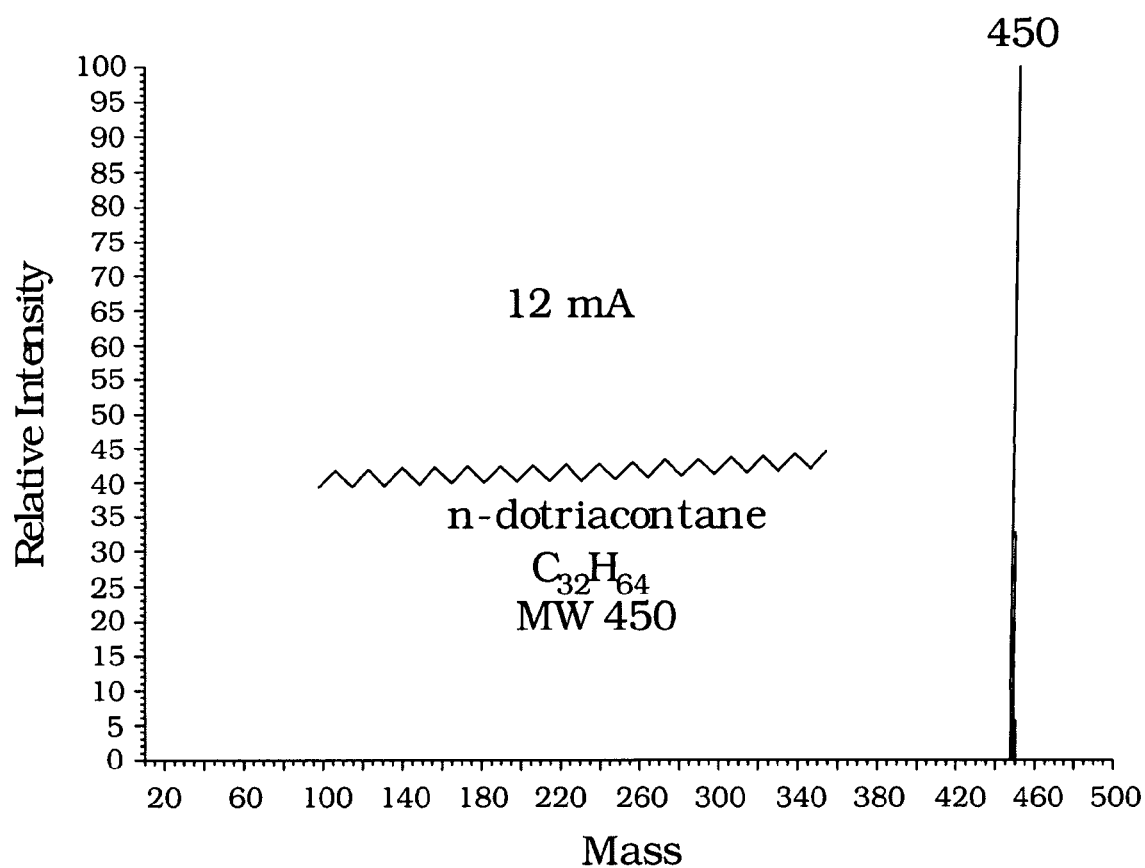
FIGS. 2A & 2B show field ionization mass spectra for dotriacontane mass spectrometer at a high (30 mA) and a low (12 mA) in-scan emitter current.
Figure 2B:
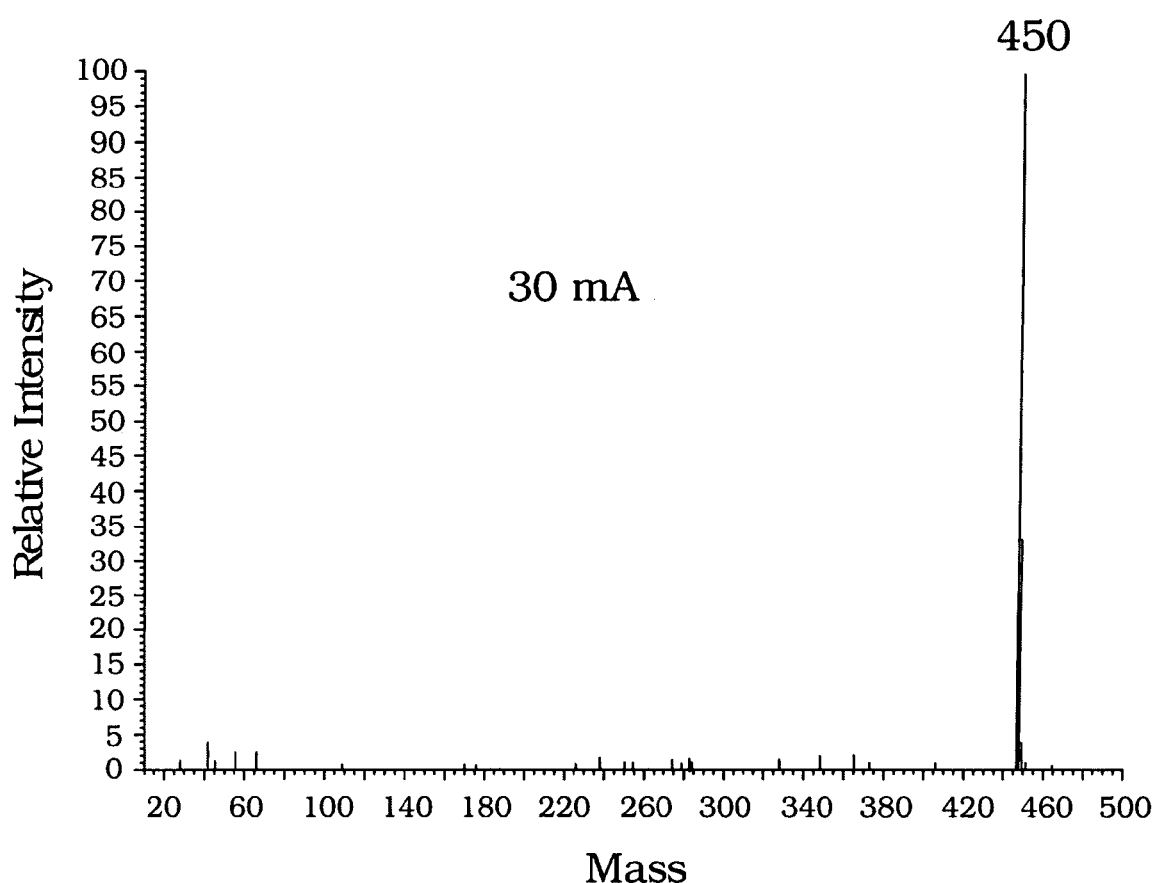
Figure 3A:
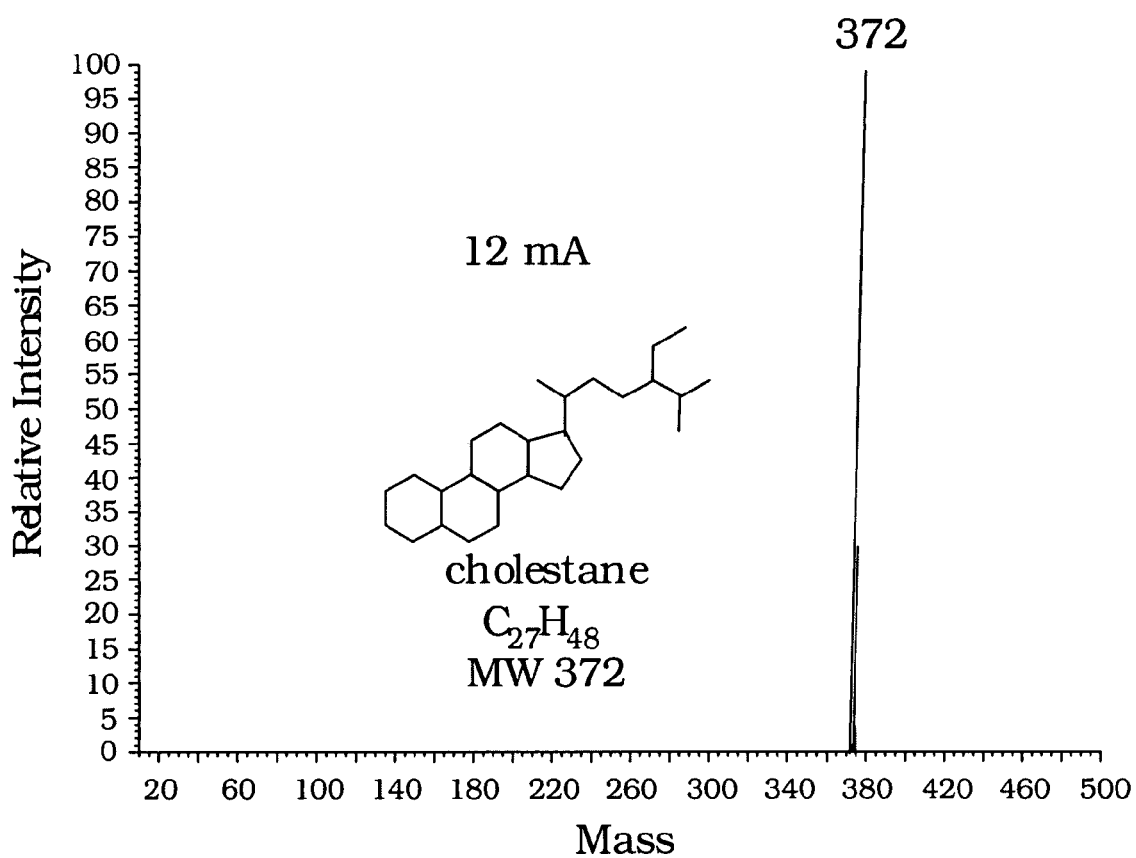
FIGS. 3A & 3B show field ionization mass spectra of cholestane at a high (30 mA) and a low (12 mA) in-scan emitter current.
Figure 3B:
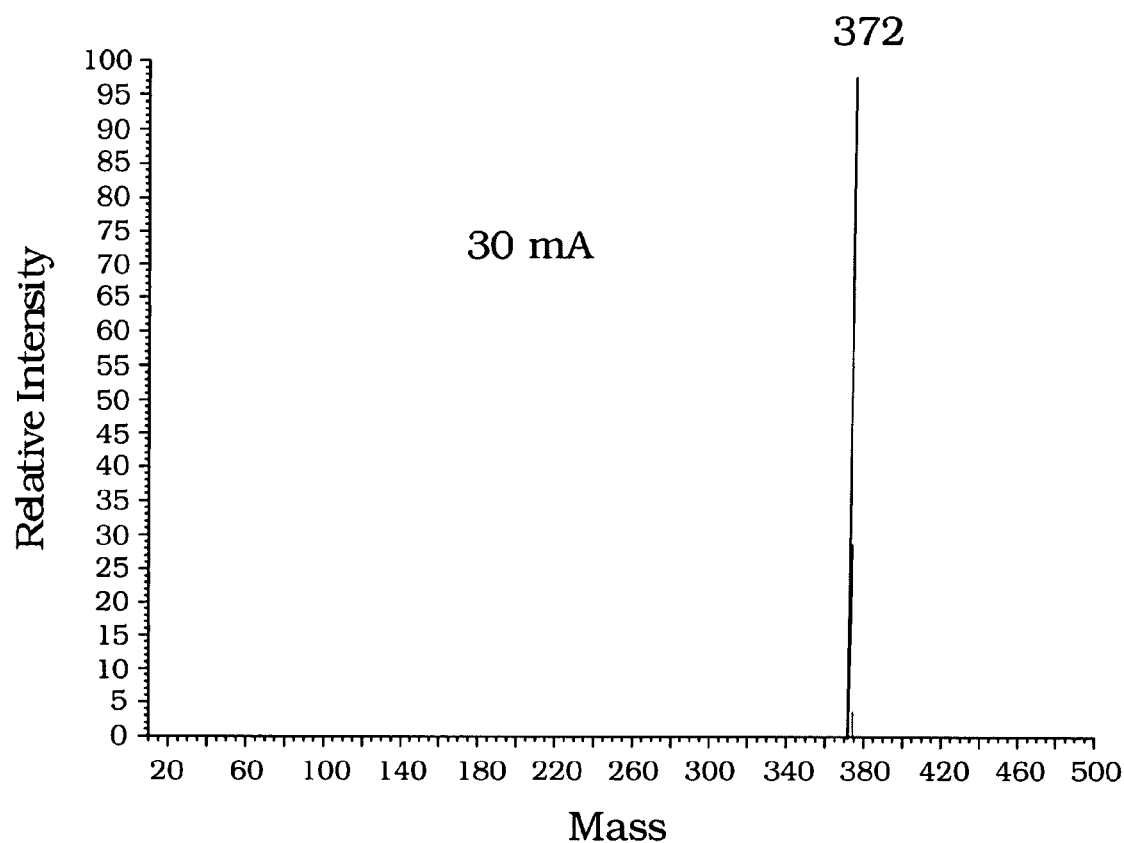

The practice of the present invention utilizes a commercially available field ionization mass spectrometer adapted to permit varying the emitter current without substantially varying the emitter potential. Referring to FIG. 1, there is shown, diagrammatically, a field ionization mass spectrometer. A high electric field is created between the emitter (10) and a counter electrode (12) by imparting a potential of about 8 to 12 kilovolts on the emitter made of a fine wire, and imparting a negative potential of about −1 to −4 kilovolts on the counter electrode. The close proximity of the emitter to the counter electrode, typically of the order of a few millimeters, produces a relatively strong electric field of the order of $10^{10}$-$10^{12}$ volts/centimeter. The emitter is typically "activated" in an organic vapor to grow dendrites around the surface of the emitter for increased ionization efficiency. A sample to be analyzed is introduced into the region between emitter and counter electrode by conventional means such as a direct insertion probe, or alternatively, a batch inlet system, a gas chromatograph (GC), A liquid chromatograph (LC), or a supercritical fluid chromatograph (SFC). In a preferred embodiment, the insertion probe may be controllably heated from room temperature to about 450° C. by conventional means. Ions formed in the field are expelled out of the ion source and accelerated by a voltage on the order of 8-10 kilovolts, whereby a mass analyzer (14), such as a magnetic type mass spectrometer is used in a conventional manner to analyze ions at high kinetic energies. In operation, the analysis apparatus is maintained under high vacuum, typically below $10^{-5}$ torr. In addition to the emitter potential, conventional FIMS apparatus apply a heater current "Ie" to the emitter, generally employed to avoid or reduce condensation of sample molecules on the emitter. The FIMS apparatus employed in the practice of the present invention, however, has been adapted to permit varying the emitter current, here shown at (20), without substantially varying the emitter potential.

For clarity in practicing this invention, there are two kinds of heating current are applied to the emitter, a conventional "flash off" emitter current, and the "in scan" emitter current. A higher current is applied to the emitter to flash off the heavy species deposited on the emitter between scans which is called between-scan current, scan flash, or flash off current. The emitter current during acquisition of mass spectral data is in-scan emitter current, By reducing the in-scan emitter current, substantially intact molecular ions of isoparaffin samples are obtained for direct field ionization mass spectrometric determination of carbon number and molecular weight distributions.

Figure 9:
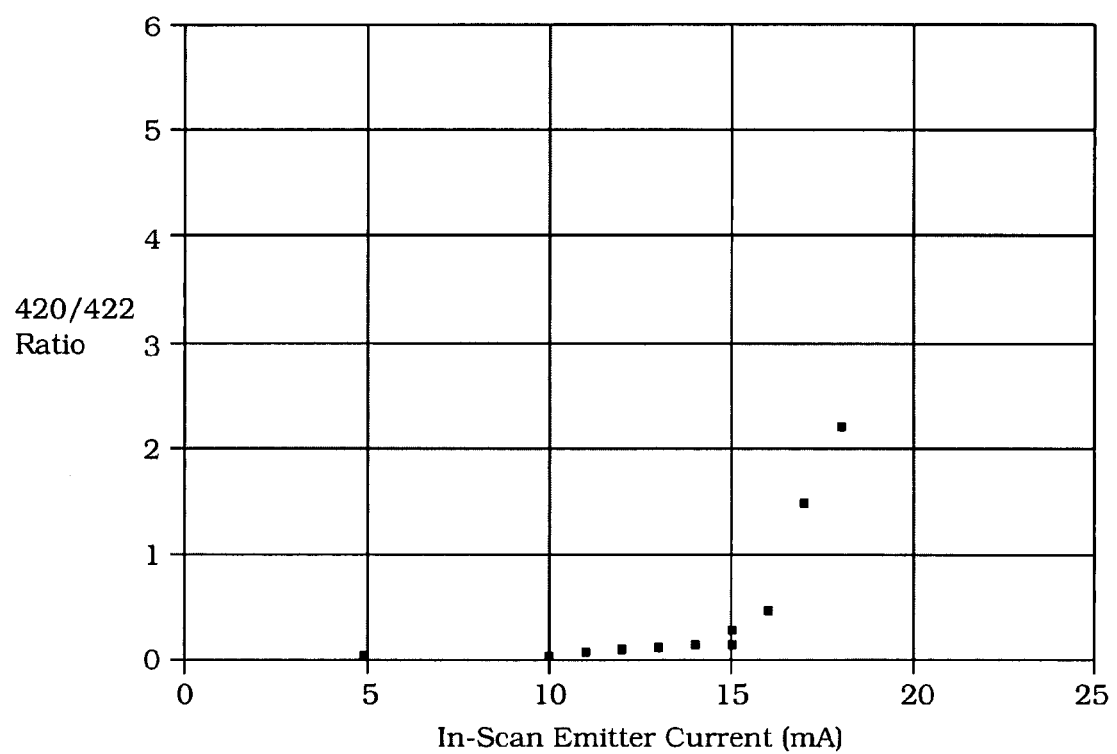
FIG. 9 is a graph of in-scan emitter current vs. 420/422 ratio of mass spectrum scans for a PAO sample.

The range of in-scan emitter currents useful in the practice of this invention will vary in relation to the surface area and configuration of the emitter. Accordingly, to establish an operating range of in-scan emitter currents, a user of this invention may vary the in-scan emitter current from relatively high values while obtaining the FI mass spectra for a known isoparaffin sample to establish an operable range of in-scan emitter current. This upper limit of the in-scan emitter current corresponds to the value that would substantially reduce or eliminate fragmentation of the isoparaffin molecular ion(s). A convenient approach to establish an upper limit of in-scan emitter currents is illustrated in FIG. 9. To obtain greater than about 50% of molecular ions for isoparaffins, the in-scan emitter current is typically set below 20 mA, preferably below about 15 mA, and most preferably below about 10 mA for a fine wire emitter having a diameter ranging from about 5 to about 50 micrometers, preferably from about five (5) micrometers to about twenty (20) micrometers. Lower fragmentation is obtainable by lower in-scan emitter currents with decreasing sensitivity. In a preferred embodiment an in-scan emitter current for isoparaffin molecular weight and carbon number determinations is less than about 20 mA, more preferably less than about 15 mA, and most preferably less than about 10 mA for an emitter ranging from about 5-50 micrometers in diameter.

The following examples illustrate embodiments of the present invention:

EXAMPLE 1

A VG-ZAB high performance mass spectrometer was fitted with a field ionization emitter from Linden ChroMas Spec. The emitter was fashioned from a tungsten wire having a nominal diameter of about five (5) micrometers. The emitter wire was "activated" by the manufacturer to produce dendrites around the wire to increase the area of high electric field. Samples for analysis are introduced via a direct insertion probe that was temperature programmable from room temperature to about 500° C. The foregoing apparatus is housed in a vacuum chamber capable of sustaining a vacuum of about $10^{-6}$ torr, by conventional means.

Commercial samples of dotriacontane ($C_{32}H_{64}$), cholestane ($C_{27}H_{48}$) and squalane ($C_{30}H_{62}$) were chosen to illustrate application of the invention to analysis of normal paraffins, naphthenes, and isoparaffins, respectively. Mass spectra were obtained for the dotriacontane and cholestane samples, first using conventional emission currents of about thirty (30) mA, followed by analysis using a low in-scan emitter current of about twelve (12) mA. The FI mass spectra obtained for dotriacontane and cholestane at high and low in-scan emitter currents are shown in FIGS. 2A, 2B, 3A, and 3B respectively. As can be seen in the drawings, there is no substantial difference between the high and low in-scan emitter current mass spectra for these samples of normal paraffins and naphthenes.

Figure 4A:
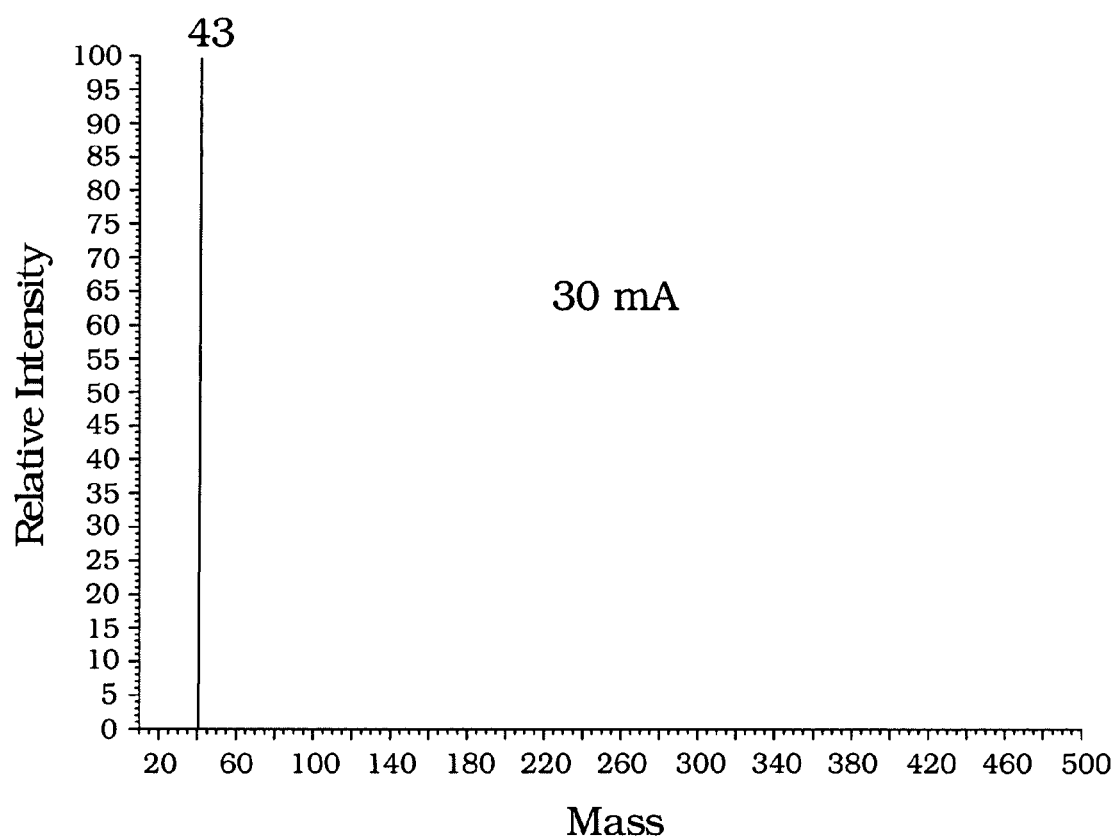
FIGS. 4A & 4B show field ionization mass spectrum of squalane, an isoparaffin, at a high (30 mA) and a low (12 mA) in-scan emitter current.
Figure 4B:
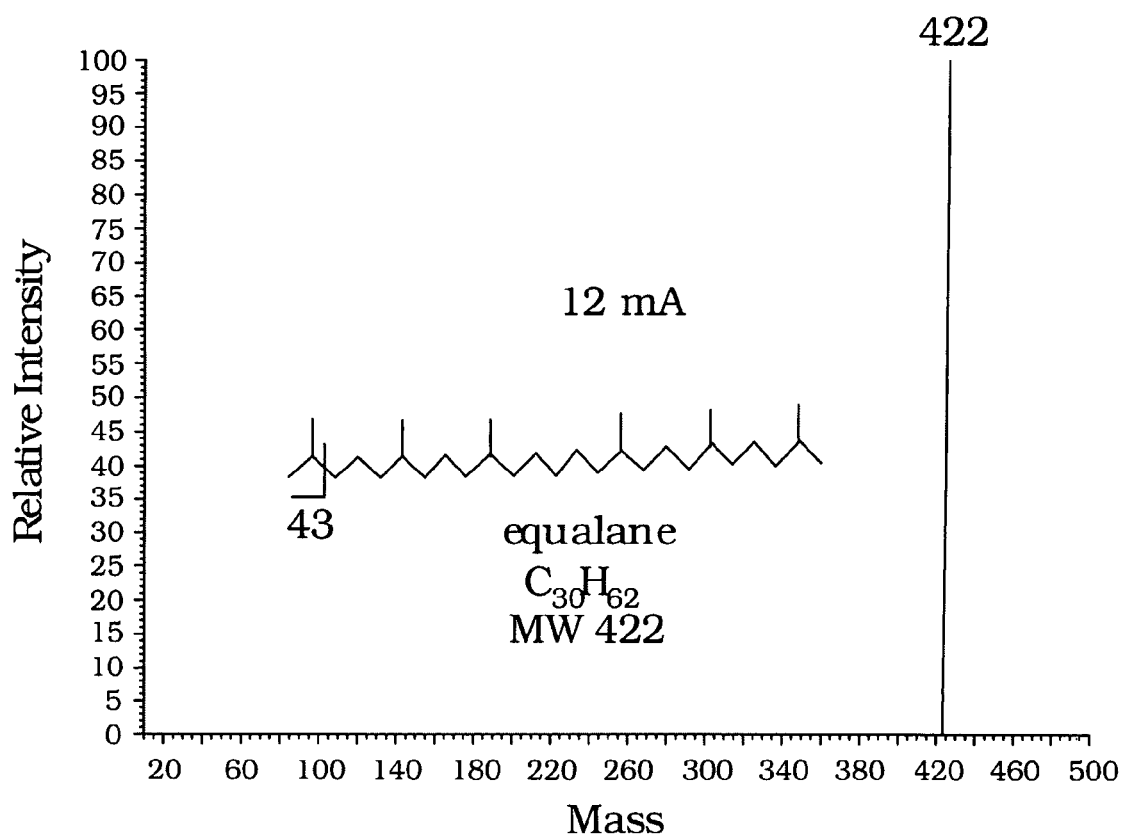

Mass spectra were then obtained for the squalane sample, which is a known highly branched isoparaffin. The mass spectrum shown in FIG. 4A is that obtained for the squalane sample using conventional emitter current levels, i.e., 30 mA for this emitter configuration. No molecular ion is obtained. The mass spectrum was then obtained using the low in-scan emitter current of the present invention. The mass spectrum of FIGS. 4B shows that molecular fragmentation has been substantially reduced or eliminated, leaving essentially the molecular ion at 422 daltons.

EXAMPLE 2

Comparative analytical techniques were used to analyze two additional commercial isoparaffin containing products. The first Sample A was a low boiling point product, having an initial boiling point of 320° F. and a dry point of 349° F. The second Sample, B, was a high boiling point product, having an initial boiling point of 523° F. and a dry point of 594° F.

Figure 5:
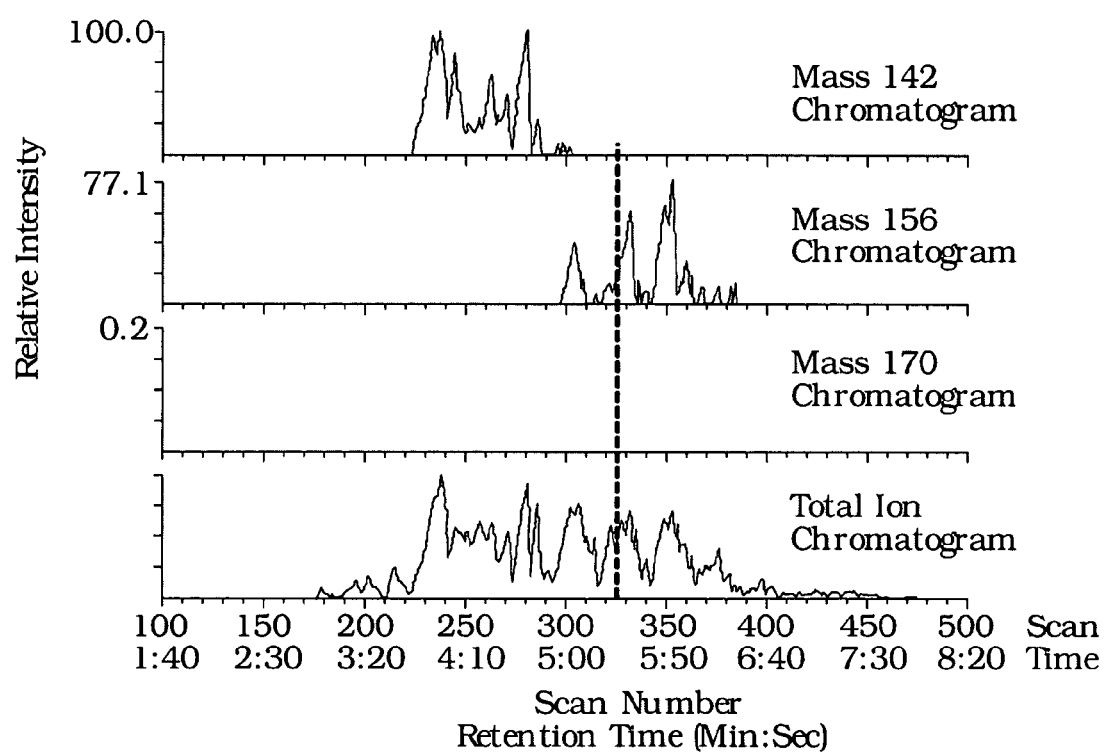
FIG. 5 traces AB&C show chromatograms of a low boiling point isoparaffin mixture.

GC/MS Chromatograms were obtained for Sample A (Isopar G), and are shown in FIG. 5. All of the components eluting off a boiling point GC column between $nC_9$ (approx. 3.0 minutes) and $nC_{11}$ (approx. 8 minutes). Chromatograms 5A (142 Daltons) and 5B (156 Daltons) show a presence of $C_{10}$ and $C_{11}$ isoparaffins, chromatogram 5C shows substantially no presence of $C_{12}$ isoparaffins (i.e. zero response in the mass 170 chromatogram). Overlap between $C_{10}$ and $C_{11}$ isoparaffins and the elution of some $C_{11}$ isoparaffins ahead of $nC_{10}$ illustrate the shortcoming of these analytical techniques for defining carbon number distribution of isoparaffins based on the retention times of normal paraffins.

Figure 6:
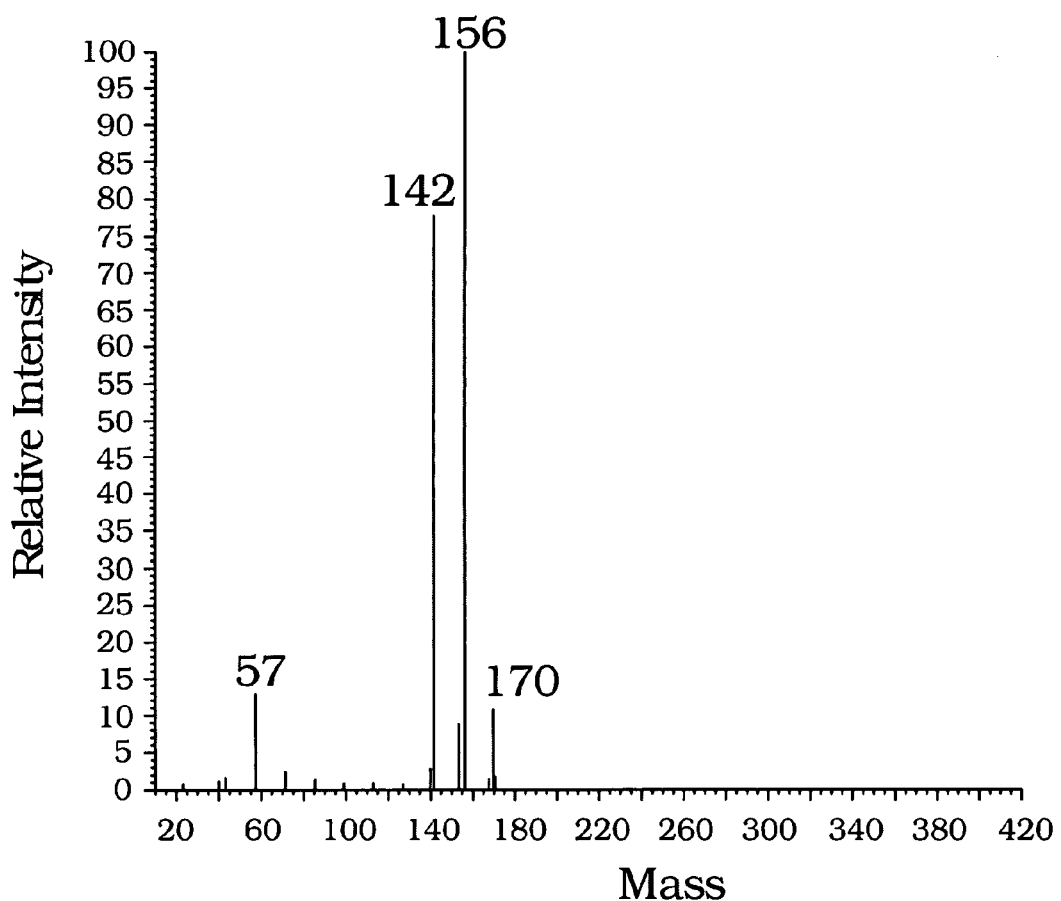
FIG. 6 shows a field ionization mass spectrum of a low boiling point isoparaffin mixture using the present invention.

Sample A was then analyzed using the techniques taught in this invention. The low in-scan emitter current mass spectrometer described in Example 1 was used to analyze Sample A. The results, shown in FIG. 6, reveal the distribution of the isoparaffins as approximately 53% $C_{11}$ isoparaffins, approximately 42% $C_{10}$ isoparaffins, and about 5% $C_{12}$ isoparaffins. Remaining composition is revealed to be $C_{10}$ to $C_{12}$ 1-ring naphthenes.

Sample B (Isopar V) was then analyzed in a similar manner. All components elute between $nC_{14}$ (approx. 14 minutes) and $nC_{20}$ (approx. 25.5 minutes) on a boiling point GC column. However, due to the severe overlap of the components, this conventional technique is unable to determine the isoparaffins.

Figure 7:
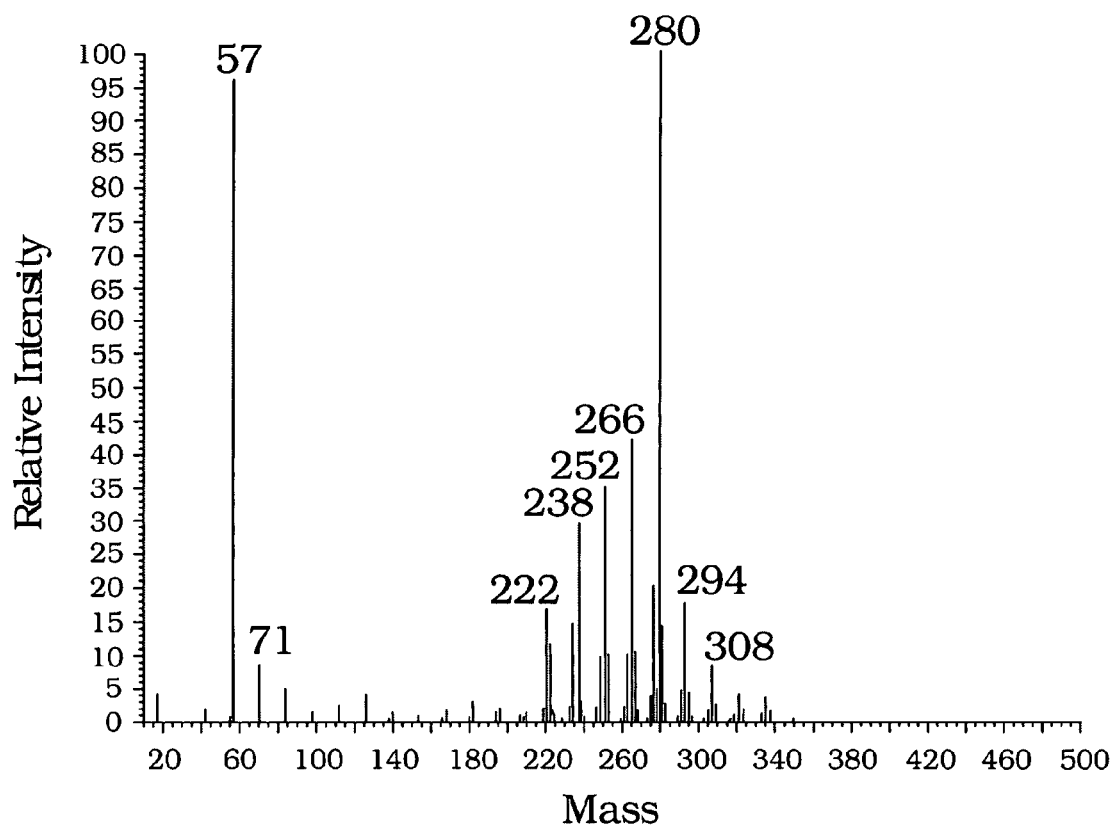
FIG. 7 shows a field ionization mass spectrum of a high boiling point isoparaffin mixture using the present invention.

Sample B was then analyzed using the low in-scan emitter current mass spectrometer. The results, shown in FIG. 7, reveal that Sample B comprises a mixture of naphthenes (greater than about 95%).

The homologous series of masses 224 (224, 238, 252, 266, 280, 294, 308, and so on) are the molecular ions of 1-ring naphthenes. It also contains lesser amounts of 2-ring naphthenes; with isoparaffins constitute minor components in the product. The intense m/z 57 peak indicates the presence of highly branched isoparaffinic structures (25%) in the Sample B (Isopar V) matrix.

EXAMPLE 3

Figure 8:
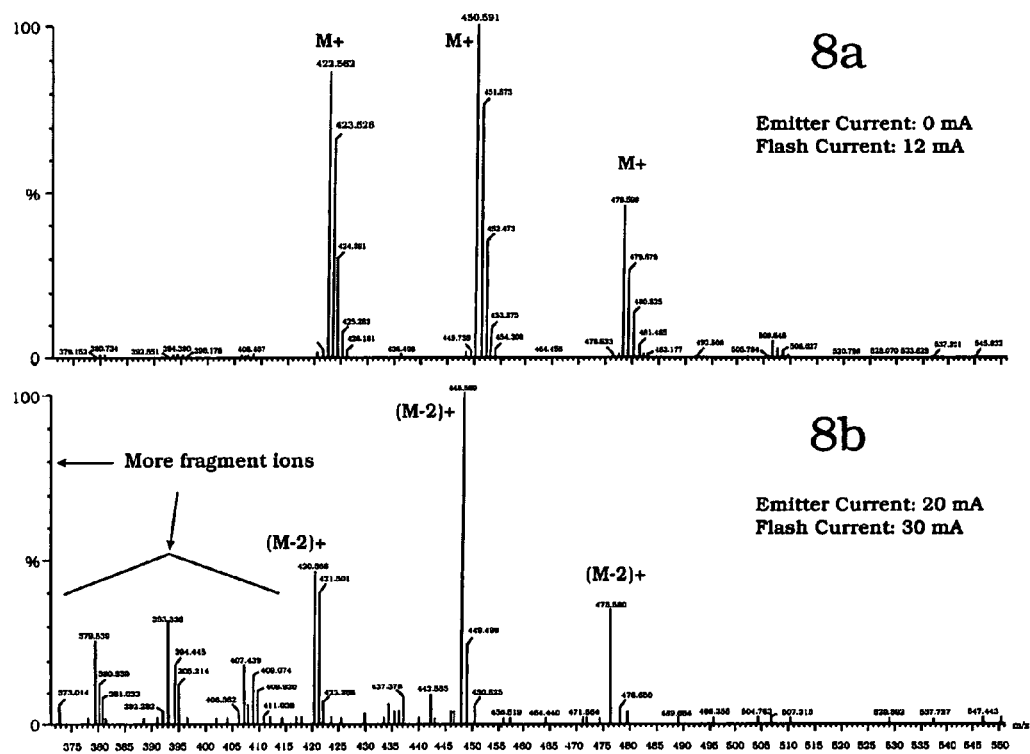
FIGS. 8a and 8b show field ionization mass spectrum of a polyalpha olefin (PAO) mixture, first using the present invention, then without the benefit of the present invention.

A 4 cSt polyalpha olefin (PAO) that contains $C_{30}$, $C_{32}$, $C_{34}$ and some $C_{36}$ isoparaffins, is examined under different emitter current conditions. The top trace of FIG. 8 shows that intact molecular ion peaks at 422, 450, 478 and 506 Da and their associated isotopic peaks are predominant at in-scan emitter current of less than about 1 mA and flash-off current at 12 mA. At a 20 mA in scan emitter current, in contrast, fragment ions are predominant. Instead of molecular ions, (M-2) and associated fragment ion peaks dominate the FIMS spectrum shown as the bottom trace of FIG. 8. The masses of these M-2 ions correspond to 1-ring cycloparaffins of the same carbon number. Artifact peaks are produced at high emitter current, leading to misidentification of acyclic paraffins as 1-ring cycloparaffins.

EXAMPLE 4

A 4 cSt polyalpha olefin (PAO) was subjected to FIMS emitter current studies using the low in-scan emitter current process taught herein. The flash-off current was about 2-12 mA higher than the in-scan emitter current. The flash-off current contributes some, but to a lesser extent than the emitter current, to molecular ion fragmentation. We used the ratio of 420 (M-2, corresponding to the $C_{30}$ cyclohexanes) to 422 (M, molecular ion of $C_{30}$ isoparaffins) to represent the extent of fragmentation. FIG. 9 illustrates that the preferred operation range of the in-scan emitter current for obtaining intact molecular ions is below about 15 mA, preferably below about 10 mA. Above about 15 mA, extensive fragmentation can occur.

What is claimed is:

1. A direct method for measuring carbon numbers and molecular weights of isoparaffins as intact molecular ions using a field ionization mass spectrometer, the method comprising reducing an in-scan emitter current in the field ionization mass spectrometer below a threshold value to substantially reduce fragmentation of isoparaffin molecular ions whereby said isoparaffins are measured directly as molecular ions.

2. The method of claim 1 wherein the in-scan emitter current is reduced below a value sufficient to reduce said fragmentation of isoparaffin molecular ions to less than about fifty (50) percent.

3. The method of claim 1 wherein the field ionization mass spectrometer used has an emitter having a diameter ranging from about 5 micrometers to about 50 micrometers and wherein said in-scan emitter current is reduced to less than about 20 mA.

4. The method of claim 3 wherein said in-scan emitter current is reduced to less than about 1 mA to about 15 mA.

5. The method of claim 4 wherein said in-scan emitter current is reduced to less than about 10 mA.

6. The method of claim 1 wherein said isoparaffins are characterized as $C_x$ isoparaffins where x is greater than about 10.

7. The method of claim 6 wherein x ranges from about 10 to about 50.

8. The method of claim 1 wherein a carbon number distribution of isoparaffins mixtures is determined by directly measuring a molecular ion distribution of the isoparaffin mixtures.

9. The method of claims 3 or 4 wherein the field ionization mass spectrometer used has an emitter having a diameter that ranges from about 5 micrometers to about 10 micrometers.

* * * * *